United States Patent
Heinonen (10) Patent No.: US 9,592,357 B2
(45) Date of Patent: Mar. 14, 2017

(54) METHOD FOR CONTROLLING A CAPACITY OF CARBON DIOXIDE REMOVER IN AN ANESTHESIA BREATHING SYSTEM AND ANESTHESIA BREATHING SYSTEM FOR VENTILATING LUNGS OF A SUBJECT

(71) Applicant: General Electric Company, Schenectady, NY (US)

(72) Inventor: Erkki Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 762 days.

(21) Appl. No.: 14/088,644

(22) Filed: Nov. 25, 2013

(65) Prior Publication Data

US 2015/0144135 A1 May 28, 2015

(51) Int. Cl.
*A61M 16/22* (2006.01)
*A61M 16/01* (2006.01)
(Continued)

(52) U.S. Cl.
CPC ......... *A61M 16/0057* (2013.01); *A61B 5/087* (2013.01); *A61B 5/0836* (2013.01);
(Continued)

(58) Field of Classification Search
CPC .......... A61M 16/0045; A61M 16/0051; A61M 16/01; A61M 16/12; A61M 16/22; A61M 2016/0039; A61M 2016/0042; A61M 2016/1025; A61M 2016/103; A61M 2016/1035; A61M 2202/0208;
(Continued)

(56) References Cited

U.S. PATENT DOCUMENTS

| | | | | |
|---|---|---|---|---|
| 4,146,887 A | * | 3/1979 | Magnante | G01N 27/16 128/202.22 |
| 4,440,162 A | * | 4/1984 | Sewell | A62B 18/088 128/202.22 |

(Continued)

FOREIGN PATENT DOCUMENTS

EP          1 579 884 A1     9/2005

*Primary Examiner* — Annette Dixon
(74) *Attorney, Agent, or Firm* — Andrus Intellectual Property Law, LLP (57) ABSTRACT

A method for controlling a capacity of a carbon dioxide remover in an anesthesia breathing system is disclosed herein. The method includes determining exhaled breathing gas flow volume of a subject in the breathing system, and determining exhaled gas flow volume removed from the breathing system. The method also includes determining carbon dioxide concentration exhaled, and calculating a data indicative of a volume of carbon dioxide removed by the carbon dioxide remover from a breathing gas flow based on the determined exhaled breathing gas flow volume, the determined exhaled gas flow volume removed from the breathing system and the determined carbon dioxide concentration. The method also includes storing the calculated data indicative of the volume of carbon dioxide removed by the carbon dioxide remover, and comparing the stored calculated data with information indicative of carbon dioxide removing capacity of the carbon dioxide remover.

20 Claims, 2 Drawing Sheets

(51) Int. Cl.
| | |
|---|---|
| *A61M 16/00* | (2006.01) |
| *A61B 5/083* | (2006.01) |
| *A61B 5/091* | (2006.01) |
| *A61B 5/087* | (2006.01) |
| *A61M 16/10* | (2006.01) |
| *A61M 16/08* | (2006.01) |
| *A61M 16/18* | (2006.01) |

(52) U.S. Cl.
CPC ......... *A61B 5/091* (2013.01); *A61M 16/0051* (2013.01); *A61M 16/01* (2013.01); *A61M 16/0891* (2014.02); *A61M 16/104* (2013.01); *A61M 16/22* (2013.01); *A61M 16/18* (2013.01); *A61M 2016/0027* (2013.01); *A61M 2016/0036* (2013.01); *A61M 2016/0039* (2013.01); *A61M 2205/3569* (2013.01); *A61M 2205/3592* (2013.01); *A61M 2205/6054* (2013.01); *A61M 2230/432* (2013.01)

(58) Field of Classification Search
CPC .. A61M 2202/0283; A61M 2205/6054; A61M 2230/432; A62B 18/088; A62B 19/00
USPC ............ 128/202.22, 202.26, 204.18, 205.12, 128/205.27, 205.28
See application file for complete search history.

(56) References Cited

U.S. PATENT DOCUMENTS

| | | | | |
|---|---|---|---|---|
| 4,578,762 | A * | 3/1986 | Wong | G01J 1/36 250/343 |
| 6,618,687 | B2 * | 9/2003 | Warkander | G01K 11/003 374/E11.002 |
| 7,987,849 | B2 * | 8/2011 | Heesch | A61M 16/0045 128/204.18 |
| 2006/0278220 | A1 | 12/2006 | Schermeier et al. | |

* cited by examiner

METHOD FOR CONTROLLING A CAPACITY OF CARBON DIOXIDE REMOVER IN AN ANESTHESIA BREATHING SYSTEM AND ANESTHESIA BREATHING SYSTEM FOR VENTILATING LUNGS OF A SUBJECT

The disclosure relates generally to a method for controlling a capacity of a carbon dioxide remover in an anesthesia breathing system and an anesthesia breathing system for ventilating lungs of a subject.

Inhalation anesthesia is delivered using a re-breathing circuit comprising an inspiratory limb through which a patient gets an inspired breathing gas from a ventilator, an expiratory limb carrying an exhaled gas back to the ventilator, a Y-piece connecting the inspiratory and expiratory limbs to a further patient limb providing a gas communication pathway to patient lungs. An expired gas comprises a lot of expensive and environment-hostile anesthesia gases. The re-breathing circuit enables recirculating the expired gas to subsequent inspiration to preserve the anesthesia gases in the circuit to lower both costs and environmental exhausts. Before re-breathing, the expired gas must be cleared from carbon dioxide (CO2) extracted from the patient lungs as waste product of a patient metabolism. This clearance is done in a CO2 absorber.

In the absorber CO2 is absorbed to soda-lime in a reaction with sodium- or potassium hydroxide. This reaction consumes the hydroxide and finally the container runs empty of the chemical and absorption is stopped. For indicating absorber consumption the absorbent is mixed with colouring agent indicating the granules running empty of their absorption capacity. This indicator reacts on pH of the absorbent, which decreases with the absorption. This colouring is however not very sensitive and color difference between absorber fully exhausted for clinical purpose and almost unused may be very small. The color change neither never occur the whole absorber, since the absorber is clinically used when even a low portion of the expired CO2 flows through but to create the color change a large pH change is needed. Such change requires a large amount of absorption and in these circumstances the CO2 flow through is already clinically unacceptable. Furthermore, coloring disappears when the absorbent dries out and user may wrongly interpret the remaining absorbent capacity.

Because of the uncertainty of the color change, clinician detects the absorbent capacity running empty measuring inspired gas CO2 concentration rise. Absorber is typically deemed clinically exhausted when the inspired gas contains 0.5% CO2. Problem in this is that information is received only when patient is connected and operation is going on whereas clinical practice would prefer solution that could confirm the anesthesia system is tested operational before patient arrival also regarding the absorber. Using exhausted absorber, inspired gas concentration rise time from normal FiO2 below 0.2% to 0.5% indicating absorber exhaust may be only 30 min to 1 hour. This means that absorbent must be changed in the middle of anesthesia, or according to regular schedule fitted to typical usage pattern. The first of these is discomfort to user and the other additional cost to the hospital.

BRIEF DESCRIPTION OF THE INVENTION

The above-mentioned shortcomings, disadvantages and problems are addressed herein which will be understood by reading and understanding the following specification.

In an embodiment, a method for controlling a capacity of a carbon dioxide remover in an anesthesia breathing system includes determining in a processing unit exhaled breathing gas flow volume of a subject in the anesthesia breathing system, and determining in the processing unit exhaled gas flow volume removed from the anesthesia breathing system. The method also includes determining in the processing unit carbon dioxide concentration exhaled by the subject, and calculating in the processing unit a data indicative of a volume of carbon dioxide removed by the carbon dioxide remover from a breathing gas flow based on the determined exhaled breathing gas flow volume, the determined exhaled gas flow volume removed from the breathing system and the determined carbon dioxide concentration. The method also includes storing in a memory unit the calculated data indicative of the volume of carbon dioxide removed by the carbon dioxide remover, and comparing in the processing unit the stored calculated data with information indicative of carbon dioxide removing capacity of the carbon dioxide remover.

In another embodiment, an anesthesia breathing system for ventilating lungs of a subject includes a ventilator for supplying a breathing gas for an inspiration and for receiving a breathing gas for an expiration, and a fresh gas mixer for supplying a fresh gas for the subject breathing. The anesthesia breathing system also includes a breathing circuit for connecting lungs of the subject, the ventilator and the gas mixer, the breathing circuit comprising an inspiration tube providing an inspiration gas including the fresh gas for the subject breathing, an expiration tube to discharge an exhaled breathing gas, and a carbon dioxide remover for removing carbon dioxide from the expiration gas. The anesthesia breathing system also includes a processing unit for determining exhaled breathing gas flow rate of the subject, determining exhaled gas flow volume removed from the anesthesia breathing system, determining carbon dioxide concentration exhaled by the subject, and calculating a data indicative of a volume of carbon dioxide removed by the carbon dioxide remover from a breathing gas flow based on the determined exhaled breathing gas flow volume, the determined exhaled gas flow volume removed from the breathing system, and the determined carbon dioxide concentration. The anesthesia breathing system also includes a memory unit for storing the calculated data indicative of the volume of carbon dioxide removed by the carbon dioxide remover. The processing unit is also configured to compare the stored calculated data with information indicative of carbon dioxide removing capacity of the carbon dioxide remover.

In yet another embodiment, a method for controlling a capacity of a carbon dioxide remover in an anesthesia breathing system includes receiving in a memory unit information indicative of carbon dioxide removing capacity of the carbon dioxide remover, and determining in a processing unit exhaled breathing gas flow volume of a subject in the anesthesia breathing system. The method also includes determining (53) in the processing unit exhaled gas flow volume removed from the anesthesia breathing system, and determining in the processing unit carbon dioxide concentration exhaled by the subject. The method also includes calculating in the processing unit a data indicative of a volume of carbon dioxide removed by the carbon dioxide remover from a breathing gas flow based on the determined exhaled breathing gas flow volume, the determined exhaled gas flow volume removed from the breathing system and the determined carbon dioxide concentration. The method also includes storing in a memory the calculated data indicative of the volume of carbon dioxide removed by the carbon dioxide remover, and comparing in the processing unit the stored calculated data with information indicative of carbon dioxide removing capacity of the carbon dioxide remover. The method also includes providing information indicative of carbon dioxide removing capacity of the carbon dioxide remover based on the comparing.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
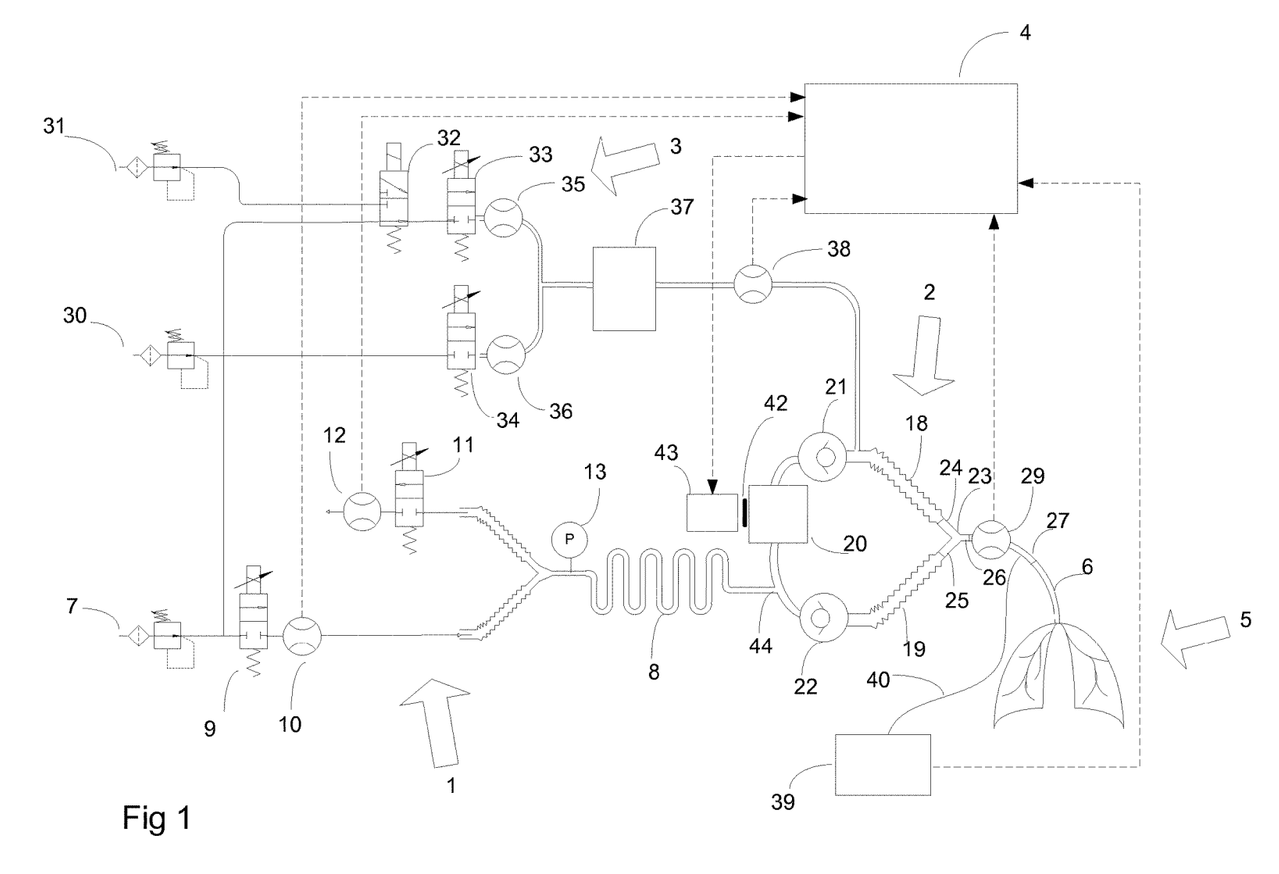
FIG. 1 illustrates a schematic diagram of an anesthesia breathing system in accordance with an embodiment.

FIG. 1 shows an anesthesia breathing system for ventilating lungs of a subject. The anesthesia breathing system may be controlling a capacity of carbon dioxide (CO2) remover. Typically this system is for monitoring carbon dioxide volume removed, for instance absorbed in a CO2 absorber. The anesthesia breathing system comprises a ventilator 1, a breathing circuit 2, a fresh gas mixer 3 and a processing unit 4, such as an absorption calculator unit. A subject 5 is connected to the breathing circuit 2 by means of an endotracheal tube 6.

In FIG. 1 the ventilator 1 is connected to a gas supply 7 for drive gas, which is typically pressurized air or sometimes also oxygen. The ventilator 1 comprises a reciprocating unit 8 for compressing gas towards lungs of the subject to facilitate the inspiration, a flow control valve 9 to control the inspired gas flow from the gas supply 7 towards the reciprocating unit 8, a flow sensor 10 such as a drive gas inspiration flow sensor for measuring a ventilator drive gas flow added for the inspiration, which flow sensor typically locates between the flow control valve 9 and the reciprocating unit 8. Further the ventilator 1 comprises an expiration valve 11 used to control the expired gas flow rate releasing the gas from the breathing circuit 2, subject 5 and reciprocating unit 8 when the subject 5 is expiring, a flow sensor 12 such as an expiration flow sensor for measuring the gas flow removed for the expiration through the expiration valve 11. The flow sensor used to measure the expiration flow can be of any type of state-of-the art flow sensor, e.g. hot wire, ultrasonic, or pressure drop over flow restrictor. Very often the ventilator 1 also comprises a ventilator pressure sensor 13 to measure a pressure of the ventilator gas upstream the reciprocating unit 8 and the ventilator 1 may be equipped with a gas supply selection (not shown) that can be used to switch the ventilator gas flow for the inspiration either manually or automatically e.g. in case the used gas gets un-pressurized.

The drive gas flow added for the inspiration and measured by the flow sensor 10 of the ventilator 1 and regulated with the flow control valve 9 may be controlled according to a control algorithm embedded in a controller device (not shown). An output of the flow sensor 10 as well as a signal of the ventilator pressure sensor 13 can be used to control the inspiration flow. The expiration flow measured by the flow sensor 12 is controlled with the expiration valve 11. When ventilating the subject, the expiration valve 11 is closed and the flow control valve 9 is opened for the inspiration. During the expiration the flow control valve 9 is closed and the expiration valve 11 is opened to control the expiration flow and pressure. This control typically is aiming for target breathing system pressure, which is measured with the pressure sensor 13.

The ventilator 1 is connected to the breathing circuit 2 with the reciprocating unit 8 for both inspired and expired gas flows. The breathing circuit 2 comprises an inspiration tube 18 for inspired gas, an expiration tube 19 for expired gas, a carbon dioxide (CO2) remover 20, such as CO2 absorber, to remove or absorb carbon dioxide from the exhaled gas coming from the subject 5, a first one way valve 21 for inspired gas in the inspiration tube 18, a second one way valve 22 for expired gas in the expiration tube 19, a branching unit 23, such as a Y-piece, having at least three limbs, one of them being an inhalation limb 24 for inspired gas, a second one being an expiration limb 25 for expired gas, a third one being a combined inspiration and expiration limb 26 for both inspired and expired gases. The inhalation limb 24 is connectable to the inspiration tube 18 and the expiration limb 25 is connectable to the expiration tube 19. The combined inspiration and expiration limb 26 of the branching unit 23 may be connectable by means of a patient tube 27 to the endotracheal tube 6 allowing the gas exchange with airways of the subject 5.

The inspiration gas flows from the reciprocating unit 8 through the CO2 remover 20 first one-way valve 21 and the inspiration tube 18 of the breathing circuit 2 to the branching unit 23 and further through the patient tube 27 and the endotracheal tube 6 to the lungs of the subject 5. The second one-way valve 22 on the expiratory tube 19 guides the gas flow direction to the inspiration tube 18 by closing the flow from the reciprocating unit 8 through the expiration tube 19. Increasing the gas volume within the lungs increases the lung pressure due to the subject lung compliance. Once the inspiration stops and the expiration valve 11 opens, the lung compliance pushes the alveolar gas through the endotracheal tube 6 and the patient tube 27 to the branching unit 23 and further through the expiration tube 19 and the reciprocating unit 8 through the expiration valve 11 and expiration flow sensor 12 measuring the gas flow leaving the breathing system. The patient tube 27 may be equipped also with a patient flow sensor 29 measuring the reciprocating inspiration- and expiration flows. A gas analyzer 39, which can be of a side-stream type or a mainstream type, measures the inspired- and expired gas concentrations. Side-stream analyzers take a sample gas flow for analysis from patient tube 27 through sampling line 40 connected to the patient tube 27 at connection point 41. Alternatively the mainstream type gas analyzer (not shown) is connected to the patient tube 27.

The most common type of gas analyzer used for CO2 monitoring is based on infrared absorption when passing through the measured gas. The gas analyzer used on any of these methods can be either mainstream type when the absorption measurement chamber is connected to patient limb directly, or sidestream type when the analyzer draws a sample flow from patient limb to a measurement chamber located distally from the patient in separate measurement module.

Traditional reciprocating unit of anesthesia ventilator comprises a bellows-in-bottle, which separates a ventilator drive gas from the circulating breathing gas. For the inspiration, outside of the bellows is pressurized with ventilator drive gas. This squeezes the bellows forcing the breathing gas within the bellows to flow towards the patient lungs. During the expiration, the drive gas pressure is released and the gas pressurized in the patient lungs flows out filling the bellows. Breathing gas is supplied to the re-breathing circuit as continuous flow using a fresh gas line supplying to inspiration line. Once the bellows is filled, further gas flow to the circuit from the patient and the fresh gas line increases the circuit pressure, which opens an over-pressure bleed valve and this further gas flows to gas scavenging.

An alternate reciprocating unit is shown in FIG. 1 to separate the drive gas and the breathing gas, which is a long gas channel between the ventilator drive gas control and the breathing circuit 2. An advantage of this alternate design over the bellows-in-bottle is a provision of continuous ventilation even if the breathing system leaks whereas with the bellows system ventilation will stop when the bellows runs empty due to leak.

The fresh gas mixer 3 for delivering a fresh gas is connected to the breathing circuit 2. The fresh gas mixer 3 is used to deliver the patient breathing gas. One or more gas supplies 7, 30, 31 is connected to the fresh gas mixer 3. The gas supply 7 is for the air as described above, the gas supply 30 is for oxygen and the gas supply 31 is for nitrous oxide. The gas mixer comprises a selector valve 32 to select either the gas supply 31 for nitrous oxide or the gas supply 7 for air, a flow regulating valve 33 for regulating either nitrous oxide or air flow, a flow regulating valve 34 for regulating oxygen flow and an anesthetic agent supply 37 such as a vaporizer for supplying anesthetic agent to anesthetize the subject 5. The fresh gas mixer 3 also comprises one or more flow sensors 35, 36, 38 for measuring the fresh gas flow added into the anesthesia system for respiration. The flow sensor 35 downstream the flow regulating valve 33 may be adapted to measure either nitrous oxide or air flow as a fresh gas, the flow sensor 36 downstream the flow regulating valve 34 may be adapted to measure oxygen flow as a fresh gas. The mixture is then further guided to the anesthetic agent supply 37 in case it is a vaporizer for adding the inhalation agent into the mixture as shown in FIG. 1. Alternatively the gas mixer 3 may be equipped with a flow sensor 38 for measuring the total gas flow of the gas mixer 3, but it is not absolutely necessary, because the total gas flow of the gas mixer 3 can be determined from other available information. If there is no flow sensor 38 downstream the anesthetic agent supply 37 the vaporized inhalation agent flow can either be measured by the anesthetic agent supply 37 itself or it is known gas flow in which case it can be based on a concentration setting of this anesthetic agent supply 37.

Carbon dioxide removers last for many patients and those may last also for days or even whole week. The anesthesia breathing system or advantageously the carbon dioxide remover 20 may have a memory unit 42 for receiving information indicative of carbon dioxide removing capacity of the carbon dioxide remover 20 and storing a calculated data indicative of a volume of carbon dioxide removed, such as the CO2 absorption volume information. The memory unit may be part of the anesthesia breathing system, typically in the anesthesia machine. Over the carbon dioxide remover usage period it may get changed without anesthesia breathing system noticing that. Therefore, in advantageous form, the consumption data may be stored on the memory unit physically connected to the carbon dioxide remover. This memory unit may be advantageously a RFID (radio frequency identification) tag mounted on the remover. Such memory unit may allow wireless communication with a transceiver device 43 for reading and storing the information disclosed hereinbefore on the carbon dioxide remover 20.

Figure 2:
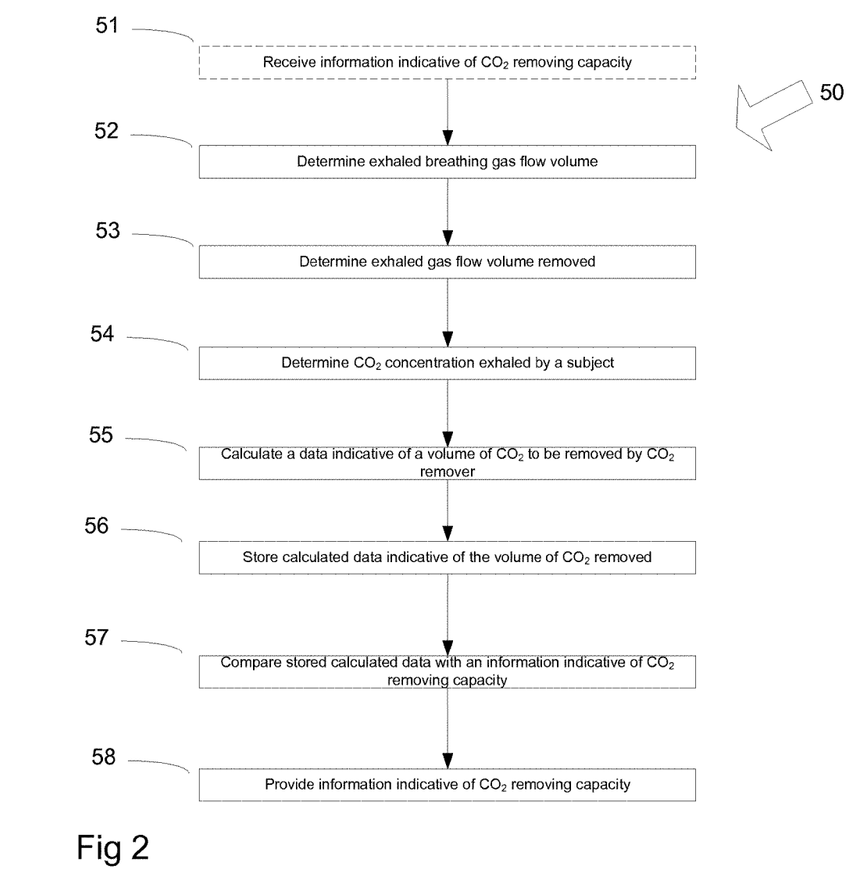
FIG. 2 is a block diagram illustrating a method in accordance with an embodiment.

Referring to FIG. 2, a block diagram illustrates a method 50 for controlling the capacity of the carbon dioxide remover 20 in the anesthesia breathing system. Information indicative of carbon dioxide removing capacity of the carbon dioxide remover is received by the memory unit 42 at an optional step 51. The user may provide this information after confirming it from a provider of the carbon dioxide remover or this information may be stored already in the factory in which case typically the carbon dioxide removers with predetermined carbon dioxide removing capacity may be used. Also it is possible that the capacity information is read for instance from the RFID tag and provided to the processing or memory unit.

At step 52 exhaled breathing gas flow volume of a subject in the anesthesia breathing system is determined in the processing unit 4. The flow rate can be measured by the flow sensors 29 or 12, which can provide the measured flow rate to the processing unit to determine exhaled breathing gas flow volume. According to step 53 exhaled gas flow volume removed from the anesthesia breathing system is determined in the processing unit. This determination can be made from the flow measurement made by at least one of the flow sensors 35, 36 and 38 provided to the processing unit 4 or alternatively as difference of the volumes measured by flow sensors 12 and 10 over breath cycle.

At step 54 carbon dioxide concentration exhaled by the subject is determined in the processing unit 4. The gas analyzer 39 can measure carbon dioxide concentration and provide the concentration information to the processing unit. At step 55 a data indicative of a volume of carbon dioxide, which may be removed by the carbon dioxide remover from a breathing gas flow, is calculated in the processing unit based on the determined exhaled breathing gas flow volume, the determined exhaled gas flow volume removed from the breathing system and the determined carbon dioxide concentration. There are two different options to make this calculation.

According to a first option a volume of exhaled carbon dioxide can be calculated in the processing unit 4 based on the determined exhaled breathing gas flow volume of the subject, and the determined exhaled carbon dioxide concentration. Further based on this calculated volume of exhaled carbon dioxide, the determined exhaled breathing gas flow volume, and the determined exhaled gas volume removed may be calculated the data indicative of the volume of carbon dioxide removed by the carbon dioxide remover from the breathing gas flow.

According to second option a volume of the gas flow intended to penetrate the carbon dioxide remover is calculated based the determined exhaled gas flow volume removed, and the determined exhaled breathing gas flow volume. The determined exhaled gas flow volume removed can simply be subtracted from the determined exhaled breathing gas flow volume. Further based on this volume of the gas flow intended to penetrate the carbon dioxide remover, and the determined carbon dioxide concentration exhaled by the subject may be calculated the data indicative of the volume of carbon dioxide removed by the carbon dioxide remover from the breathing gas flow.

The calculated data indicative of the volume of carbon dioxide removed by the carbon dioxide remover is provided to the memory unit 42, where it is stored at step 56 and summed up previous data, if such data already exists in the memory unit, indicating carbon dioxide already removed by the carbon dioxide remover. This stored data can be provided to the processing unit to compare at step 57 the stored calculated data with the information indicative of carbon dioxide removing capacity of the carbon dioxide remover 20, which information can be received for instance already in the factory or at the optional step 51.

Further information indicative of carbon dioxide removing capacity of the carbon dioxide remover is provided by the processing unit at step 58. Information indicative of carbon dioxide removing capacity may be at least one of remaining carbon dioxide removing capacity of the carbon dioxide remover, carbon dioxide removing capacity of the carbon dioxide remover already exploited, a relative usage rate of the carbon dioxide removing capacity, and a remaining usage time of said carbon dioxide remover. This information may be provided to the user as an audible or visible signal, or it may be provided to any component which may take a measure to change the carbon dioxide remover to another fresh remover.

The steps 52-56 regarding to determining, calculating and storing steps may occur periodically, typically on breath-to-breath basis or on time basis e.g. using minute ventilation and scavenged/fresh gas flow rate. Naturally step 57 with or without step 58 may also occur periodically, typically on breath-to-breath basis or on time basis e.g. using minute ventilation and scavenged/fresh gas flow rate.

The determination of the data indicative of the removed CO2 volume is based on the system property that all CO2 is coming from the subject expiration. This subject expiration volume then divides to re-breathed volume ($V_{RB}$) for the next breath and scavenged or removed gas volume through the expiration valve 11. Removed CO2 volume for single breath is then the product of re-breathed volume and rebreathed concentration ($C_{RB}$). To increase the calculation accuracy towards the end of absorber life-time, the CO2 volume penetrating through the absorber can be subtracted. This is however not quite necessary since at the point where significant penetration takes place, the absorber is already close to the end of its life-time.

To calculate CO2 volume removed in the carbon dioxide remover 20, the gas analyzer 39 is used to measure inspired carbon dioxide (FiCO2) and end tidal carbon dioxide EtCO2 concentrations. Two different set of equations can be derived depending on the breathing circuit configuration:

1. The first embodiment includes alternatives where the expiration flow sensor measured fresh gas flow delivered during expiration
   a. the fresh gas flow from the fresh gas mixer 3 is delivered downstream the first one-way valve 21 as indicated on FIG. 1 and the expiration flow sensor 12 is on expiration pathway downstream the branching unit 23,
   b. the fresh gas flow is delivered upstream the first one-way valve 21 and the expiration flow sensor 12 is on expiration pathway downstream the connection 44, which connection is between the breathing circuit 2 and the reciprocating unit 8.
2. The second embodiment includes alternatives where the expiration flow sensor 12 measures only subject expiration flow during expiration
   a. the fresh gas flow is delivered upstream the first one-way valve 21 and the expiration flow sensor 12 is on expiration pathway upstream connection 44,
   b. the expiration flow sensor is connected on patient tube 27 as indicated with number 29.

The First Embodiment

The expiration flow sensor 12 is used to measure the output volume ($V_{out}$) from the breathing circuit 2. The flow sensor information, which is either from the flow sensor 38 or together the flow sensors 35, 36, and the anesthetic agent supply 37 flow is used to determine the breathing gas volume in the output volume Following equations can be written:

$$V_{exp} = V_{out} - V_{FG}^{exp}, \quad (1)$$

where $V_{exp}$ is the subject expired volume and $V_{FG}^{exp}$ is a fresh gas volume delivered during expiration period. This equation designates that during time of subject expiration, the flow measured with expiration flow sensor 12 is derived both from the patient and from the fresh gas mixer. For the subject expired volume can be written as well $$V_{exp} = V_{RB} + V_{FG}^{in}, \quad (2)$$

where $V_{RB}$ is a rebreathed volume and $V_{FG}^{in}$ is fresh gas volume delivered during inspiration period. Equation 2 designates the breath volume comprises of fresh gas portion delivered during inspiration and the rebreathed volume ($V_{RB}$). Solving eq. 1 and 2 for $V_{RB}$ and combining the fresh gas volume components with ($V_{FG} = V_{FG}^{exp} + V_{FG}^{in}$) gives:

$$V_{RB} = V_{out} - V_{FG}, \quad (3)$$

where $V_{FG}$ is a fresh gas volume delivered during the breath. Expiration flow comprises of two components: A dead space expiration and an alveolar expiration. The dead space expiration is the volume coming from subject airways, endotracheal tube 6 and patient tube 27. This represents the dead space gas volume ($V_d$) remaining at gas flow channel between branching unit 23 and the subject alveoli at the end of inspiration, and does not include CO2 since that is not mixing with the alveolar gas. The alveolar expiration ($V_{alv}$) gas comes from active lung area and includes CO2 in concentration of EtCO2. Average expired concentration ($C_{RB}$) is then $$\begin{aligned} C_{RB} &= \frac{V_{alv}}{V_{exp}} \cdot EtCO_2 \\ &= \frac{V_{exp} - V_d}{V_{exp}} \cdot EtCO_2 \\ &= \left(1 - \frac{Vd}{Vexp}\right) \cdot EtCO_2 \\ &= (1 - V_D) \cdot EtCO_2, \end{aligned} \quad (4)$$

where $V_D$ is relative proportion of the dead space volume to the whole expiration volume.

The single breath absorbed volume is then the product of rebreathed volume and rebreathed concentration ($C_{RB}$)

$$\begin{aligned} V_{abs}^{CO_2} &= V_{RB} \cdot C_{RB} \quad (5)\\ &= (V_{out} - V_{FG}) \cdot \left(1 - \frac{Vd}{Vexp}\right) \cdot EtCO_2 \\ &= (V_{out} - V_{FG}) \cdot \left(1 - \frac{Vd}{V_{out} - V_{FG}^{exp}}\right) \cdot EtCO_2 \quad (6)\\ &= (V_{out} - V_{FG}) \cdot (1 - V_D) \cdot EtCO_2 \quad (7) \end{aligned}$$

Quantitatively, the fresh gas flow rate and the removed carbon dioxide volume have inverse relationship. Equations 5-7 indicate this having the $V_{FG}$ linearly reducing the first multiplier. Breathing gas leak reduces the measured $V_{out}$ and respectively carbon dioxide removing volume. $V_{out}$ has positive relationship to the first multiplier, thus the reduction reduces also the carbon dioxide removing volume.

If needed, the CO2 penetration through the carbon dioxide remover 20, which occurs close to the end of usage time can be calculated from measured inspired CO2 concentration:

$$FiCO_2 = \frac{C_{RB}^{out} \cdot V_{RB}}{V_{RB} + V_{FG}^{in}} \qquad (8)$$

$$C_{RB}^{out} = \frac{FiCO_2 \cdot (V_{RB} + V_{FG}^{in})}{V_{RB}}, \qquad (9)$$

where $C_{RB}^{out}$ is the CO2 concentration of the gas flow leaving the carbon dioxide remover 20. Multiplying this with the $V_{RB}$ gives the CO2 flow penetrating the carbon dioxide remover 20, which can be subtracted from equation 5-7 to compensate for the penetration.

The Second Embodiment

Difference to the first embodiment is that in this configuration the fresh gas flow is not passing through the expiration flow sensor during expiration time, i.e. all the measured flow is coming from the subject exhalation. Thus, the exhalation flow sensor does not detect the fresh gas flow during expiration $V_{FG}^{exp}$. In this circumstance the expiration flow sensor gives directly the $V_{exp}$ of equation 2. For rebreathed volume we get instead of equation 3

$$V_{RB} = V_{exp} - V_{FG}^{in} \qquad (3a)$$

Expired concentration equation 4 remains unchanged, thus we get for the alternative forms of removed CO2 volume equations $$V_{abs}^{CO2} = V_{RB} \cdot C_{RB} \qquad (5a)$$

$$= (V_{exp} - V_{FG}^{in}) \cdot \left(1 - \frac{Vd}{Vexp}\right) \cdot EtCO_2$$

$$= (V_{exp} - V_{FG}^{in}) \cdot \left(1 - \frac{Vd}{V_{out} - V_{FG}^{exput}}\right) \cdot EtCO_2 \qquad (6a)$$

$$= (V_{exp} - V_{FG}^{in}) \cdot (1 - V_D) \cdot EtCO_2 \qquad (7a)$$

Compensation for CO2 penetration through the carbon dioxide remover 20 occurs similarly as on the first embodiment.

Equations 5-7, 5a-7a, present the removed CO2 volume for single breath in various forms. Summing up the removed volume to all breaths gives the total removed volume. Total carbon dioxide removing capacity of the carbon dioxide remover 20 depends on the type and amount of the material, such as absorbent, used to remove carbon dioxide. When the anesthesia breathing system has available an information indicative of at least one of remaining carbon dioxide removing capacity of the carbon dioxide remover and carbon dioxide removing capacity of the carbon dioxide remover already exploited, that can include also an information to a clinician, which is a relative usage rate (used/total), carbon dioxide removing capacity remaining (total−used), relative capacity remaining ((total−used)/total) or during anesthesia when knowing the breath-wise carbon dioxide removing rate the usage time remaining ((total−used)($V_{abs}^{CO2} \cdot RR$) where RR is the respiration rate in breaths/minute. The remaining carbon dioxide removing capacity of the carbon dioxide remover may indicate the remaining total removing volume of the carbon dioxide remover. The carbon dioxide removing capacity of the carbon dioxide remover already exploited may indicate the removed volume of the carbon dioxide remover already exploited.

If needed, the usage time left can be increased by increasing the fresh gas flow rate. This can be used to match the usage time left with estimated duration of the operation and hereby avoiding absorber change in the middle of case. Although this is not very economical on long term considering the increase of cost-dominant inhalation anesthesia agent, on short term this can be convenient to the user and also cost-effective if un-scheduled carbon dioxide remover change is avoided.

As explained hereinbefore embodiments disclose a method to calculate a volume of carbon dioxide (CO2) removed, which may be removed e.g. by absorbing carbon dioxide into an absorbing material, in a carbon dioxide remover, such as an absorber.

When knowing the nominal capacity usage rate can be calculated already before anesthesia. During anesthesia, when knowing the therapy conditions, even the time remaining can be informed to the user. With this information clinician may tune the therapy settings in to preserve remaining capacity and to avoid absorber change in the middle of anesthesia.

Absorbers last for many patients and those may last also for days or even whole week. The calculated absorbed volume can be stored in the anesthesia machine memory, but over the carbon dioxide remover usage period the carbon dioxide remover may get changed without anesthesia system noticing that. Therefore, advantageously the consumption data is stored on the memory unit physically connected to the carbon dioxide remover. Such memory can utilize e.g. wireless RFID technology.

The volume of CO2 breathed out by the patient can be calculated as the integral of expiration flow and respective gas concentration. This integral is known as CO2 production and expressed typically as CO2 volume in a minute period of time. Alternatively, this integral can be estimated as product of the expired gas volume and average concentration. A third alternative is to identify alveolar expiration volume by subtracting from the expired gas volume the volume of anatomic dead-space and multiplying the remaining alveolar expiration volume with measured end-tidal CO2 (EtCO2) concentration. On this third alternative the anatomic dead-space can be estimated from patient size or measured with the gas analyzer.

During ventilation patient expired gas flow carrying the CO2 divides between the re-circulated flow that needs to be cleaned from CO2 by the absorber- and scavenged flows. In calculation of the removed, such as absorbed amount of CO2, the CO2 enriched gas flow flowing through the carbon dioxide remover is needed. It may be advantageous to subtract from the measured patient expiration flow the scavenged flow. The magnitude of the scavenged flow can be measured with a scavenging flow sensor. Alternatively that can be estimated from the fresh gas flow value, since the amount of gas in the breathing system remains constant, i.e. the amount of gas removed (scavenged) equals the amount added (=fresh gas flow). Multiplying the re-circulated flow with the respective gas concentration gives the CO2 flow to the carbon dioxide remover. Integral of this flow subtracted by the CO2 flow passing the carbon dioxide remover gives the removed CO2 volume. Because the clinically functional carbon dioxide remover removes practically all the CO2 from the flow passing the carbon dioxide remover, the CO2 flow passing the carbon dioxide remover can be assumed to zero. Alternatively that can be measured if the anesthesia system is equipped with appropriate sensors. The removed CO2 concentration can be estimated from gas analyzer readings. At maximum that equals to end tidal carbon dioxide (EtCO2) and more accurately that equals to EtCO2 multiplied by dilution factor of the anatomic dead-space.

Alternatively, the carbon dioxide remover flow can be determined by subtracting the fresh gas flow from the inspired gas flow. Multiplying this with the removed CO2 concentration gives the removed CO2 volume. Measurement of expiration flow provides, however, an advantage over this in connection to breathing system leak. Because the most common leak occurs at patient connection, the measured expiration flow value decreases and thus the re-circulated exhalation volume decreases as well. The replacement gas for the leak is free from CO2 and thus does not contribute on absorption.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for controlling a capacity of a carbon dioxide remover in an anesthesia breathing system, said method comprising:
    determining in a processing unit exhaled breathing gas flow volume of a subject in said anesthesia breathing system;
    determining in said processing unit exhaled gas flow volume removed from said anesthesia breathing system;
    determining in said processing unit carbon dioxide concentration exhaled by the subject;
    calculating in said processing unit a data indicative of a volume of carbon dioxide removed by said carbon dioxide remover from a breathing gas flow based on said determined exhaled breathing gas flow volume, said determined exhaled gas flow volume removed from the breathing system and said determined carbon dioxide concentration;
    storing in a memory unit said calculated data indicative of the volume of carbon dioxide removed by said carbon dioxide remover; and
    comparing in said processing unit said stored calculated data with information indicative of carbon dioxide removing capacity of said carbon dioxide remover.

2. The method according to claim 1, wherein said calculating comprises calculating a volume of exhaled carbon dioxide based on said determined exhaled breathing gas flow volume of the subject and said determined exhaled carbon dioxide concentration, and wherein said calculating the data indicative of the volume of carbon dioxide removed by said carbon dioxide remover from the breathing gas flow is based on this calculated volume of exhaled carbon dioxide, said determined exhaled breathing gas flow volume, and said determined exhaled gas flow volume removed.

3. The method according to claim 1, wherein said calculating comprises calculating a volume of a gas flow intended to penetrate said carbon dioxide remover based on said determined exhaled gas flow volume removed and said determined exhaled breathing gas flow volume, and wherein said calculating the data indicative of the volume of carbon dioxide removed by the carbon dioxide remover from the breathing gas flow is based on this calculated volume of the gas flow intended to penetrate said carbon dioxide remover, and said determined carbon dioxide concentration exhaled by the subject.

4. The method according to claim 1, further comprising receiving in a memory unit said information indicative of carbon dioxide removing capacity of said carbon dioxide remover.

5. The method according to claim 1, further comprising providing an information indicative of carbon dioxide removing capacity of said carbon dioxide remover based on said comparing.

6. The method according to claim 5, wherein said information indicative of carbon dioxide removing capacity of said carbon dioxide remover comprises at least one of remaining carbon dioxide removing capacity of said carbon dioxide remover, carbon dioxide removing capacity of said carbon dioxide already exploited, a relative usage rate of the carbon dioxide removing capacity, and a remaining usage time of said carbon dioxide remover.

7. The method according to claim 1, wherein said determining the exhaled breathing gas flow volume of the subject, said determining exhaled gas flow volume removed from said anesthesia breathing system, said determining carbon dioxide concentration exhaled by the subject; said calculating the data indicative of the volume of carbon dioxide removed by said carbon dioxide remover from a breathing gas flow, and said storing said calculated data are configured to be made one of periodically, a breath-to-breath basis and on time basis.

8. The method according to claim 1, wherein said comparing the stored calculated data with the information indicative of carbon dioxide removing capacity of said carbon dioxide remover is configured to be made one of periodically, a breath-to-breath basis and on time basis.

9. The method according to claim 5, wherein said providing the information indicative of carbon dioxide removing capacity of said carbon dioxide remover is configured to be made one of periodically, a breath-to-breath basis and on time basis.

10. The method according to claim 2, wherein said calculating the volume of exhaled carbon dioxide is configured to be performed by multiplying said determined exhaled breathing gas flow volume of the subject and said determined carbon dioxide concentration, which is an average concentration of exhaled breathing gas, and summing up the products over single subject expiration.

11. The method according to claim 2, further comprising determining carbon dioxide free volume representing the gaseous common connection for inspired and exhaled breathing gas before lungs of the subject and wherein said calculating the volume of exhaled carbon dioxide is configured to be performed by subtracting said carbon dioxide free volume, and multiplying the difference with said determined carbon dioxide concentration exhaled by the subject.

12. The method according to claim 1, wherein said determining exhaled gas flow volume removed from said anesthesia breathing system is equal to a fresh gas flow volume added to said anesthesia breathing system to replace exhaled gas flow volume removed from said anesthesia breathing system.

13. The method according to claim 1, wherein said storing said calculated data indicative of the volume of carbon dioxide removed by said carbon dioxide remover is configured to be summed up previous existing data in said memory unit indicating carbon dioxide already removed by said carbon dioxide remover.

14. An anesthesia breathing system for ventilating lungs of a subject comprising:
   a ventilator for supplying a breathing gas for an inspiration and for receiving a breathing gas for an expiration;
   a fresh gas mixer for supplying a fresh gas for the subject breathing;
   a breathing circuit for connecting lungs of the subject, said ventilator and said gas mixer, said breathing circuit comprising an inspiration tube providing an inspiration gas including the fresh gas for the subject breathing an expiration tube to discharge an exhaled breathing gas; and a carbon dioxide remover for removing carbon dioxide from the expiration gas;
   a processing unit for determining exhaled breathing gas flow rate of the subject in said anesthesia breathing system; determining exhaled gas flow volume removed from said anesthesia breathing system; determining carbon dioxide concentration exhaled by the subject; calculating a data indicative of a volume of carbon dioxide removed by said carbon dioxide remover from a breathing gas flow based on said determined exhaled breathing gas flow volume, said determined exhaled gas flow volume removed from the breathing system and said determined carbon dioxide concentration; and
   a memory unit for storing said calculated data indicative of the volume of carbon dioxide configured to be removed by said carbon dioxide remover;
   wherein said processing unit is configured to compare said stored calculated data with information indicative of carbon dioxide removing capacity of said carbon dioxide remover.

15. The anesthesia breathing system according to claim 14, wherein said processing unit is configured to provide said information indicative of carbon dioxide removing capacity of said carbon dioxide remover based on the comparison.

16. The anesthesia breathing system according to claim 14, wherein said memory unit is configured to receive information indicative of carbon dioxide removing capacity of said carbon dioxide remover.

17. The anesthesia breathing system according to claim 15, wherein said information indicative of carbon dioxide removing capacity of said carbon dioxide remover comprises at least one of remaining carbon dioxide removing capacity of said carbon dioxide remove, carbon dioxide removing capacity of said carbon dioxide already exploited, a relative usage rate of the carbon dioxide removing capacity, and a remaining usage time of said carbon dioxide remover.

18. The anesthesia breathing system according to claim 14, wherein said processing unit is configured to calculate a volume of exhaled carbon dioxide based on said determined exhaled breathing gas flow volume of the subject and said determined exhaled carbon dioxide concentration, and wherein said calculated data indicative of the volume of carbon dioxide removed by said carbon dioxide remover from the breathing gas flow is based on this calculated volume of exhaled carbon dioxide, said determined exhaled breathing gas flow volume, and said determined exhaled gas volume removed.

19. The anesthesia breathing system according to claim 14, wherein said processing unit is configured to calculate a volume of a gas flow intended to penetrate said carbon dioxide remover based on said determined exhaled gas flow volume removed and said determined exhaled breathing gas flow volume, and wherein said calculated data indicative of the volume of carbon dioxide removed by said carbon dioxide remover from the breathing gas flow is based on this calculated volume of the gas flow intended to penetrate said carbon dioxide remover, and said determined carbon dioxide concentration exhaled by the subject.

20. A method for controlling a capacity of a carbon dioxide remover in an anesthesia breathing system, said method comprising:
   receiving in a memory unit information indicative of carbon dioxide removing capacity of said carbon dioxide remover;
   determining in a processing unit exhaled breathing gas flow volume of a subject in said anesthesia breathing system;
   determining in said processing unit exhaled gas flow volume removed from said anesthesia breathing system;
   determining in said processing unit carbon dioxide concentration exhaled by the subject;
   calculating in said processing unit a data indicative of a volume of carbon dioxide removed by said carbon dioxide remover from a breathing gas flow based on said determined exhaled breathing gas flow volume, said determined exhaled gas flow volume removed from the breathing system and said determined carbon dioxide concentration;
   storing in a memory unit said calculated data indicative of the volume of carbon dioxide removed by said carbon dioxide remover;
   comparing in said processing unit said stored calculated data with information indicative of carbon dioxide removing capacity of said carbon dioxide remover; and
   providing information indicative of carbon dioxide removing capacity of said carbon dioxide remover based on said comparing.

* * * * *